US006660743B1

(12) United States Patent
Cances et al.

(10) Patent No.: US 6,660,743 B1
(45) Date of Patent: Dec. 9, 2003

(54) THERAPEUTIC AQUEOUS COMPOSITION CONTAINING A HEXAHYDRO-5-PYRIMIDINAMINE COMPOUND AND A POLYALKOXYLATED FATTY ALCOHOL

(75) Inventors: Joël Cances, Livert (FR); Jacques Munerot, Saint Jean de la Ruella (FR)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/890,344

(22) PCT Filed: Jan. 22, 2000

(86) PCT No.: PCT/EP00/00487

§ 371 (c)(1),
(2), (4) Date: Jul. 26, 2001

(87) PCT Pub. No.: WO00/48598

PCT Pub. Date: Aug. 24, 2000

(30) Foreign Application Priority Data

Feb. 19, 1999  (EP) .............................................. 99400408

(51) Int. Cl.$^7$ .............................................. A61K 31/505
(52) U.S. Cl. ....................................................... 514/256
(58) Field of Search ........................................ 514/256

(56) References Cited

U.S. PATENT DOCUMENTS

| 4,206,198 A | 6/1980 | Schmolka ..................... 424/49 |
| 4,774,078 A | 9/1988 | Curtis et al. .................. 424/52 |
| 4,814,334 A | * 3/1989 | Salkin ........................ 514/256 |

FOREIGN PATENT DOCUMENTS

| EP | 0408174 | 1/1991 |
| WO | WO 9209283 | 6/1992 |

* cited by examiner

*Primary Examiner*—Dwayne C. Jones
*Assistant Examiner*—C. Delacroix-Muirheid
(74) *Attorney, Agent, or Firm*—Darryl C. Little; Evan J. Federman

(57) ABSTRACT

The invention provides a therapeutic aqueous composition comprising: (i) a therapeutically effective amount of a hexahydro-5-pyrimidinamine compound, e.g. hexetidine; (ii) a salification acidic compound; and (iii) a polyalkoxylated fatty alcohol. The composition shows enhanced stability.

31 Claims, No Drawings

THERAPEUTIC AQUEOUS COMPOSITION CONTAINING A HEXAHYDRO-5-PYRIMIDINAMINE COMPOUND AND A POLYALKOXYLATED FATTY ALCOHOL

BACKGROUND OF THE INVENTION

1. Field of the Invention

This invention relates to a therapeutic aqueous composition containing an hexahydro-5-pyrimidinamine compound and a polyalkoxylated fatty alcohol, together with a salification compound. The therapeutic composition has antimicrobial and/or antiseptic efficacy and may take the form of either an oral topical or non-oral topical composition.

2. Description of the Related Art

Hexahydro-5-pyrimidinamine compounds (5-amino-hexahydro-pyrimidine), such as hexetidine (1,3-bis(2-ethylhexyl) hexahydro-5-methyl-5-pyrimidinamine), are well known in the art for their broad spectrum antimicrobial activity and their antiseptic activity. These hexahydro-5-pyrimidinamine compounds are used in aqueous-based compositions for topical application to treat skin and body cavity infections. For example, these antimicrobial and/or antiseptic compositions are used in the treatment of oral infections such as gingivitis, sore throat, oral ulcers, periodontal disease, and for the control of mouth odor, and in the treatment of other topical infections such as cervical vaginal infections, ear infections, nasal pharyngitis, and epidermal phytoses.

Hexetidine, however, has long been known to lack stability. The hexahydro-5-pyrimidinamine ring system in hexetidine can be cleaved thermally and hydrolytically to produce the open-chain compound triamine and the condensed bicyclic heterocycle hexedine, see G. Satzinger et al., *Analytical Profiles of Drug Substances*, 7, pp. 277–295, Academic Press, 1978. Therefore, the stability of hexetidine is uncertain.

WO-A-9209283 discloses that the stability of hexetidine compositions has been improved through the use of aqueous buffer solutions in conjunction with an anionic surfactant. Examples of these surfactants include POE sorbitan fatty acid esters (e.g. of the Tween® series) and POE castor oil derivatives. These compositions however suffer from some drawbacks. The solubilization of hexetidine is achieved thanks to the surfactant, but high amounts of surfactant may inhibit the antimicrobial activity of hexetidine. Also, the stability is still not sufficient for all intended applications.

U.S. Pat. No. 4,206,198 discloses a dentifrice composition which contains a foam producing amount of a nonionic surfactant and hexetidine. The nonionic surfactant is an ethoxylated adduct of a C-15 or C-16 fatty alcohol. These compositions however do not contain a major proportion of water and do not contain the hexetidine compound under a solubilized form (i.e. as salt form). The ethoxylated adduct of a C-15 or C-16 fatty alcohol would thus not appear as a useful candidate for solubilizing hexetidine in aqueous compositions, notably in compositions to be administrated per os.

It would be advantageous to further enhance both the solubility and the stability of hexetidine in aqueous compositions.

SUMMARY OF THE INVENTION

This invention is directed to a therapeutic aqueous composition comprising:
(i) a therapeutically effective amount of a hexahydro-5-pyrimidinamine compound, preferably hexetidine;
(ii) a salification acidic compound; and
(iii) a polyalkoxylated fatty alcohol.

The compositions of this invention are advantageously stable compositions that provide antimicrobial and/or antiseptic efficacy.

DETAILED DESCRIPTION OF THE INVENTION

This invention relates to the discovery that hexahydro-5-pyrimidinamine compounds can be solubilized thanks to the combined effect of:
(i) salification using an acidic compound;
(ii) micelles formation using polyalkoxylated fatty alcohol as a surfactant;
(iii) solvatation using an ol, if needed.

In the following, unless otherwise stated, all percentages are expressed in weight by volume (w/v) of the composition.

Hexahydro-5-pyrimidinamine Compounds

The hexahydro-5-pyrimidinamine compounds employed in this invention have antimicrobial and/or antiseptic efficacy. Any non-toxic hexahydro-5-pyrimidinamine compound may be employed. Suitable non-toxic therapeutically effective hexahydro-5-pyrimidinamine compounds are disclosed in U.S. Pat. No. 837,463 and U.S. Pat. No. 4,141,968, the disclosures of which are incorporated by reference herein. The hexahydro-5-pyrimidinamine compounds are either commercially available or may be readily prepared by one of ordinary skill in the art. The preferred antimicrobial and/or antiseptic hexahydro-5-pyrimidinamine compound is hexetidine (1,3-bis(2-ethylhexyl) hexahydro-5-methyl-5-pyrimidinamine).

Hexetidine has an unusual affinity for tissue. When applied topically, hexetidine adheres to tissue and is not eliminated prematurely from the site of action either physiologically or by pathological secretions. Hexetidine has a broad antibacterial spectrum which makes it very useful in preparations for topical application to skin and body cavity infections.

A therapeutically effective amount of an antimicrobial and/or antiseptic hexahydro-5-pyrimidinamine compound is present in the therapeutic composition of this invention. In a preferred embodiment, the hexahydro-5-pyrimidinamine compound is present in the therapeutic composition in an amount from about 0.025% to about 2.0%, preferably from about 0.05% to about 0.3%.

In the following, the description will be given with hexetidine as an exemplary compound of hexahydro-5-pyrimidinamine compounds, but it shall be understood that the following description applies mutatis mutandis to any of these hexahydro-5-pyrimidinamine compounds.

Polyalkoxylated Fatty Alcohol

The surfactant used in the present invention is a polyalkoxylated fatty alcohol. This type of surfactant is well-known in the art and is the adduct of alkyleneoxide (AO) with a fatty alcohol.

One polyalkoxylated fatty alcohol useful in the present invention can be represented by the formula:

$$R\text{—}(OA)_n\text{—}OH \qquad (I)$$

where:
R is an alkyl radical corresponding to the fatty alcohol and may comprise from 10 to 24 carbon atoms, preferably from 12 to 18 carbon atoms;
A is an alkylene radical comprising from 2 to 4 carbon atoms, preferably 2 carbon atoms, such that the individual OA units may be the same or different, preferably the same, and where the OA units may be present as a block proximate to the radical R or randomly distributed through the length of the chain;
n is comprised between 2 and 100, preferably between 10 and 40.

Preferred polyalkoxylated fatty alcohols, notably those of formula (I) above, are those which are saturated.

Examples of fatty alcohols include lauryl alcohol, cetyl alcohol, stearyl alcohol, cetostearyl alcohol, myristyl alcohol; the preferred alcohol is lauryl alcohol.

Preferred surfactants, notably those of formula (I) above, are those having a high HLB value, such as an HLB value greater than 15.

The amount of surfactant used in the composition can vary within broad limits; it should be noted that the amount of surfactant that is used in not limited by the influence on the therapeutic properties of hexetidine, as would be in the case of Tween®. The surfactant is used in an amount sufficient to solubilize therapeutically effective amounts of hexetidine. In general, the surfactant will be present in the composition of the invention in an amount from about 0.005% to about 5%, preferably from about 0.08% to about 2%.

Salification Acidic Compound

The salification acidic compound used in the compositions of the invention serves for forming a (partial) salt of hexetidine and thus serves for solubilizing the hexetidine compound, inasmuch as the acidic component will salify the hexetidine and will form a salt, which is more readily solubilized thanks to the surfactant of the invention. The salification compound originates from an acid, which can be either organic or mineral.

Any acidic compound can be used, such as citric acid, phosphoric acid, hydrochloric acid, tartaric acid, acetic acid, propionic acid, pyruvic acid, aspartic acid, glycolic acid, and the like can be used. Preferred acids are the citric acid, phosphoric acid and hydrochloric acid, while citric acid is the most preferred acid.

The amount of salification acidic component is such that the acidic component will form a (partial) salt with hexetidine and also such that the desired pH value is obtained. In general, it can represent up to about 1%, preferably it is comprised between 0.01% and about 0,5%. According to one embodiment, the amount of acidic component, expressed in mole per mole of hexetidine, is comprised between about 0.5 and about 1.

Aqueous Composition

The aqueous solution comprises water as a major ingredient; water thus represents in general at least 60%, preferably more than 70%.

Another main ingredient or secondary major ingredient may also be present. This secondary major ingredient is an organic solvent, preferably an hydroxylated solvent or "ol", which is a compound containing at least one hydroxyl group.

Said hydroxylated solvent or ol can be an alcohol or a polyol. Examples of alcohol include ethanol, isopropyl alcohol, etc. Examples of polyol include propylenegycol, glycerin, polyethyleneglycol, etc.

The amount of the organic solvent, preferably the hydroxylated solvent or ol, in the solution can vary within broad limits, depending on the final use of the composition (e.g. alcohol should be present at limited amounts in an ingestible composition). For oral compositions, the amount of ol can be up to 30% (v/v); when an alcohol is used, the amount thereof is preferably between about 2 and 10% (v/v) while when a polyol is used, the amount thereof is preferably between about 8 and 25% (v/v).

According to one embodiment, a spray comprises a polyol and is free of alcohol while according to another embodiment, a mouthwash or mouth rinse comprises an alcohol.

The aqueous compositions of the invention may also contain a buffer. Buffers are solutions to which limited amounts of a strong acid or strong base may be added without causing a significant change in the pH value of the solution. A buffer solution usually contains two components, such as a weak acid and a salt of a weak acid, a mixture of an acid salt with the normal salt, or a mixture of two acid salts. Suitable buffer solutions in the present invention include citric acid-sodium citrate solution, phosphoric acid-sodium phosphate solution, acetic acid-sodium acetate, and mixture thereof. A preferred buffer comprises citric acid-sodium citrate (obtained by mixing citric acid and sodium hydroxide).

The amount of buffer component can represent up to about 1%, preferably it is comprised between 0.01% and about 0,5%. The exact ratio of components in the buffer solution to obtain a specific pH value (after salification of the hexetidine compound) is well known in the art and needs no further explanation.

The pH of the aqueous compositions of the invention can be comprised between about 4 and about 7.5, most preferably between about 5.0 and about 7.5.

Excipients and Various Forms of the Composition

The therapeutic composition may be used or formulated with pharmaceutically acceptable carriers such as topical vehicles (non-oral and oral) and ingestible vehicles to prepare a wide variety of topical and ingestible pharmaceutical compositions to suit particular applications. Non-oral topical compositions employ non-oral topical vehicles, such as creams, gels, foams, ointments and sprays, which are intended to be applied to the skin or body cavity and are not intended to be taken by mouth. Oral topical compositions employ oral vehicles such as mouthwashes, rinses, oral sprays, suspension, and dental gels, which are intended to be taken by mouth but are not intended to be ingested. Ingestible compositions employ ingestible or partially ingestible vehicles such as confectionery bulking agents which include hard and soft confectionery such as lozenges, tablets, toffees, nougats, suspensions, chewy candies, and chewing gums.

The instant therapeutic compositions may also contain conventional additives normally employed in those products. Conventional additives include humectants, plasticizers, softeners, mineral adjuvants, antioxidants, coloring agents, sweetening agents, flavoring agents, emollients, lubricants, stabilizers, further emulsifier, fluorine providing compounds, dyes, perfumes, etc., provided the additives do not interfere with the therapeutic properties of the pyrimidinamine compound.

EP-A-0408174, WO-A-9209283 and WO-A-9728805, disclose the list of possible excipients, as well as the list of all possible forms of compositions. These references also provide all methods to prepare and manufacture all possible forms of compositions. The skilled man will revert to these publications and patents for carrying out the invention in the selected area.

For example, for the preparation of oral compositions, one can use the following multi-stage: (i) dissolution of the polyalkoxylated fatty alcohol with part of the water; (ii) dissolution of the acidic component and hexetidine in the solution of step (i); and (iii) mixing of the solution of step (ii) with the remainder of water. The additives can be added at selected stages. Dissolution and/or dilution can be carried out at elevated temperature, room temperature or low temperature, depending of the various ingredients.

In a preferred embodiment, the mouthwash or rinse oral composition will comprise (1) hexetidine in an amount from about 0.025% to about 1%, and (2) the surfactant in an amount from about 0.005% to about 2.5%. In a more preferred embodiment, the mouthwash or rinse oral composition will comprise (1) hexetidine in an amount from about 0.05% to about 0.5%, and (2) the surfactant in an amount from about 0.05% to about 0.5%, and most preferably will comprise (1) hexetidine in an amount from about 0.08% to about 0.15%, and (2) the surfactant in an amount from about 0.08% to about 0.2%. In this embodiment, the mouthwash or rinse oral composition preferably contains an alcohol, preferably ethanol, in an amount between about 2 and 10%.

In a preferred embodiment, the oral spray composition will comprise (1) hexetidine in an amount from about 0.05% to about 2%, and (2) the surfactant in an amount from about 0.05% to about 5%. In a more preferred embodiment, the oral spray composition will comprise (1) hexetidine in an amount from about 0.1% to about 0.5%, and (2) the surfactant in an amount from about 0.2% to about 3%, and most preferably will comprise (1) hexetidine in an amount from about 0.15% to about 0.3%, and (2) the surfactant in an amount from about 0.5% to about 2%. In this embodiment, the oral spray composition preferably contains a polyol, preferably glycerin, in an amount between about 8 and 25%, and is preferably free of alcohol.

The present invention is further illustrated by the following examples which are not intended to limit the effective scope of the claims.

EXAMPLES

In the following examples, the antimicrobial activity is determined by measuring the activity on Staphylo aureus, while the microbiological contamination is determined in accordance with the French Pharmacopeia test. In the examples, "POE" is used to indicate that the compound is polyethoxylated, and the number immediately following "POE" indicates the number of ethylene oxide molecules per molecule of compound.

Example 1

The following "base solution" is prepared:

| Component | Amount (g) |
| --- | --- |
| Citric Acid | 7 |
| Glycerin | 2000 (*) |
| Sodium Saccharinate | 10 |
| Demineralized Water | 7913 |
| Total | 9930 |

(*) the density of glycerin being 1.260, the glycerin is present in the aqueous base solution at a v/v percentage of about 17% and at a w/v percentage of about 20%.

The base solution is mixed with the surfactant and hexetidine (the last two components having been previously admixed). The final solution has the following composition:

| Component | Amount (g) | Percentage (w/v) |
| --- | --- | --- |
| Base solution | 148.2 | 98.8 |
| Surfactant | 1.5 | 1 |
| Hexetidine | 0.3 | 0.2 |
| Total | 150 | 100 |

The surfactant used is either a polyethoxylated lauryl alcohol with 23 ethylene oxide molecules or a polyethoxylated cetostearyl alcohol with 33 ethylene oxide molecules, having HLB values of 16.9 and 18.0, respectively.

The final pH was 5.01 and 4.96, respectively. In both cases the final was clear (0.57 and 0.77 NTU, respectively). NaOH (5% solution) is then added (about 0.5 ml) to the clear solutions in order to adjust the pH to a value of 7. In both cases the solution remained clear.

Example 2

The following compositions are prepared, using conventional mixing apparatus.

| Component | Amount (g) | Percentage (w/v) |
| --- | --- | --- |
| Citric Acid | 1.4 | 0.07 |
| Glycerin | 400 | 20 |
| Sodium Saccharinate | 2 | 0.1 |
| Hexetidine | 4 | 0.2 |
| Surfactant | 20 | 1.0 |
| Sodium Hydroxide (5% solution) | q.s. to pH = 7 | Variable |
| Demineralized Water | q.s. to 2000 ml | q.s. 100 |

The following table gives, for each surfactant, the HLB value.

| Surfactant | HLB value |
| --- | --- |
| Polysorbate 20 | 16.7 |
| Hydrogenated POE 40 Castor Oil | 13.5 |
| Hydrogenated POE 45 Castor Oil | 14.0 |
| Ethoxylated Castor Oil | 12.6 |
| POE 23 Lauryl Alcohol | 16.9 |
| POE 20 Cetyl Alcohol | 15.7 |

The following table gives, for each surfactant, the amount of sodium hydroxide solution added, as well as the initial and final pH values. The solution are numbered from E1 to E6.

| Solution | Surfactant | Init. pH | NaOH amount | Final pH |
| --- | --- | --- | --- | --- |
| E1 | Polysorbate 20 | 4.90 | 9.5 | 7.03 |
| E2 | Hydrogenated POE 40 Castor Oil | 5.21 | 8.7 | 7.00 |
| E3 | Hydrogenated POE 45 Castor Oil | 5.70 | 7.7 | 7.02 |
| E4 | Ethoxylated Castor Oil | 5.07 | 9.5 | 7.00 |
| E5 | POE 23 Lauryl Alcohol | 5.20 | 7.3 | 7.00 |
| E6 | POE 20 Cetyl Alcohol | 5.06 | 8.0 | 7.02 |

The above was repeated, except that the intended final pH was 5. To that effect, more citric acid is used, i.e. the initial solution has a concentration of 0.09% (instead of 0.07% in the previous tests). The solutions are numbered from A1 to A6.

| Solution | Surfactant | Init. pH | NaOH amount | Final pH |
| --- | --- | --- | --- | --- |
| A1 | Polysorbate 20 | 4.54 | 2.7 | 5.00 |
| A2 | Hydrogenated POE 40 Castor Oil | 4.53 | 2.7 | 5.00 |
| A3 | Hydrogenated POE 45 Castor Oil | 4.61 | 2.4 | 5.00 |
| A4 | Ethoxylated Castor Oil | 4.55 | 2.5 | 5.00 |
| A5 | POE 23 Lauryl Alcohol | 4.57 | 2.3 | 5.00 |
| A6 | POE 20 Cetyl Alcohol | 4.58 | 2.3 | 5.01 |

Turbidity was measured after 10 days. The results are summarized in the following table:

| Solution | NTU | Solution | NTU |
| --- | --- | --- | --- |
| E1 | 1.09 | A1 | 0.77 |
| E2 | 3.5 | A2 | 2.3 |
| E3 | 3.4 | A3 | 2.3 |
| E4 | 44 | A4 | 3.1 |
| E5 | 0.59 | A5 | 0.46 |
| E6 | 0.86 | A6 | 0.68 |

The above results are evidencing that only the polyethoxylated fatty alcohols provide clear solutions at both pH=5 and pH=7.

Example 3

Oral Spray

The following oral spray is prepared using a multi-stage process and apparatus. The pH is about 7.

| Component | Amount (g) | Percentage (w/v) |
| --- | --- | --- |
| Sodium Hydroxide | 0.215 | 0.02 |
| Citric Acid | 0.700 | 0.07 |
| Sodium saccharinate | 0.400 | 0.04 |
| Demineralized Water | 815.625 | q.s. to 100 |
| Glycerin | 200.000 | 20.0 (*) |
| Hexetidine | 2.060 | 0.2 |
| POE 23 Lauryl Alcohol | 14.000 | 1.4 |
| Flavor | 13.000 | 1.3 |

(*) density of 1.260, equivalent to 15.9% v/v.

Example 4

Mouth Rinse

The following mouth rinse is prepared using a multi-stage process and apparatus. The pH is about 5.

| Component | Amount (g) | Percentage (w/v) |
| --- | --- | --- |
| Azorubine | 40.000 | 4.00 |
| Flavor | 1.410 | 0.14 |
| Citric Acid | 0.420 | 0.04 |
| Ethanol (96°) (*) | 40.000 | 4.0 (*) |
| Sodium saccharinate | 0.220 | 0.02 |
| Demineralized Water | 942.980 | q.s. to 100 |
| Hexetidine | 1.050 | 0.1 |
| POE 23 Lauryl Alcohol | 1.400 | 0.14 |

(*) density of 0.806, equivalent to 5.0% v/v.

Both the oral spray and the mouth rinse are stable for 6 months at storage temperatures of 4° C. and 30° C. No microbiological contamination could be detected, at both storage temperatures. Both the oral spray and the mouth rinse have a bactericide activity on Staphylo aureus.

The invention being thus described, it will be obvious that the same may be varied in many ways. Such variations are not to be regarded as a departure from the spirit and scope of the invention and all such modifications are intended to be included within the scope of the following claims.

What is claimed is:

1. A therapeutic aqueous composition comprising:

(i) a therapeutically effective amount of a hexahydro-5-pyrimidinamine compound;

(ii) a salification acidic compound; and
(iii) a polyalkoxylated fatty alcohol
wherein the compositions are clear after 10 days as defined by NTU values of less than 1.09.

2. The composition of claim 1, wherein the hexahydro-5-pyrimidinamine compound is hexetidine.

3. The composition of claim 2, wherein the hexahydro-5-pyrimidinamine compound is present in an amount from about 0.025% to about 2.0%.

4. The composition of claim 3, wherein the hexahydro-5-pyrimidinamine compound is present in an amount from about 0.05% to about 0.3%.

5. The composition of claim 1 wherein the salification acidic compound comprises citric acid.

6. The composition of claim 5, wherein the salification acidic compound is present in amount between 0.01% and about 0.5%.

7. The composition of claim 1, further comprising a buffer.

8. The composition of claim 7, wherein the buffer comprises citric acid-sodium citrate.

9. The composition of claim 1, having a pH value between about 4 and about 7.5.

10. The composition of claim 9, having a pH value between about 5.0 and about 7.5.

11. The composition of claim 1, wherein the polyalkoxylated fatty alcohol has a HLB value greater than 15.

12. The composition of claim 11, wherein the polyalkoxylated fat alcohol is saturated.

13. The composition of claims 11, wherein the polyalkoxylated fatty alcohol is represented by the formula:

$$R—(OA)_n—OH \qquad (I)$$

where:
R is an alkyl radical corresponding to the fatty alcohol and comprises from 10 to 24 carbon atoms;
A is an alkylene radical comprising from 2 to 4 carbon atoms, such that the individual OA units may be the same or different, and where the OA units may be present as a block proximate to the radical R or randomly distributed through the length of the chain;
n is comprised between 2 and 100.

14. The composition of claim 13, wherein the polyalkoxylated fatty alcohol is represented by the formula:

$$R—(OA)_n—OH \qquad (1)$$

where:
R comprises from 12 to 18 carbon atoms;
A is an alkylene radical comprising 2 carbon atoms; and
n is comprised between 10 and 40.

15. The composition of claims 14, wherein the fatty alcohol is lauryl alcohol.

16. The composition of claims 1, wherein the polyalkoxylated fatty alcohol is present in an amount from about 0.005% to about 5%.

17. The composition of claim 16, wherein the polyalkoxylated fatty alcohol is present in an amount from about 0.08% to about 2%.

18. The composition of claims 1, wherein the aqueous composition comprises an hydroxylated solvent in an amount up to 30 w/v %.

19. The composition of claim 18, wherein the hydroxylated solvent is an alcohol.

20. The composition of claim 19, wherein the alcohol is ethanol.

21. The composition of claim 18, wherein the hydroxylated solvent is present at an amount between about 2 and 10% (v/v).

22. The composition of claim 1, which is a mouthwash or a mouth rinse.

23. The composition of claim 22, which comprises (1) the hexahydro-5-pyrimidinamine compound in an amount from about 0.05% to about 0.5%, and (2) the polyalkoxylated fatty alcohol in an amount from about 0.05% to about 0.5%.

24. The composition of claim 23, which comprises (1) the hexahydro-5-pyrimidinamine compound in an amount from about 0.08% to about 0.15%, and (2) the polyalkoxylated fatty alcohol in an amount from about 0.08% to about 0.2%.

25. The composition of claim 18, wherein the hydroxylated solvent is a polyol.

26. The composition of claim 25, wherein the polyol is glycerin.

27. The composition of claim 25, wherein the polyol is present at an amount between about 8 and 25 (v/v).

28. The composition of claim 25, which is an oral spray.

29. The composition of claim 28, free of alcohol.

30. The composition of claim 28, which comprises (1) the hexahydro-5-pyrimidinamine compound in an amount from about 0.1% to about 0.5%, and (2) the polyalkoxylated fatty alcohol in an amount from about 0.2% to about 3%.

31. The composition of claim 30, which comprises (1) the hexahydro-5-pyrimidinamine compound in an amount from about 0.15% to about 0.3%, and (2) the polyalkoxylated fatty alcohol in an amount from about 0.5% to about 2%.

* * * * *